(12) United States Patent
Sugita et al.

(10) Patent No.: US 7,534,222 B2
(45) Date of Patent: May 19, 2009

(54) INJECTION DEVICE

(75) Inventors: Kouichi Sugita, Osaka (JP); Hiroshi Matsumoto, Hyogo (JP)

(73) Assignee: JCR Pharmaceuticals., Ltd, Hyogo (JP)

( * ) Notice: Subject to any disclaimer, the term of this patent is extended or adjusted under 35 U.S.C. 154(b) by 0 days.

(21) Appl. No.: 11/604,900

(22) Filed: Nov. 28, 2006

(65) Prior Publication Data
US 2007/0185439 A1 Aug. 9, 2007

(30) Foreign Application Priority Data
Nov. 29, 2005 (JP) .............................. 2005-344094

(51) Int. Cl.
*A61M 37/00* (2006.01)
(52) U.S. Cl. .......................... 604/82; 604/135; 604/207
(58) Field of Classification Search .................. 604/82, 604/92, 232–234, 86, 89, 91, 134, 135, 207
See application file for complete search history.

(56) References Cited

U.S. PATENT DOCUMENTS

| | | | |
|---|---|---|---|
| 4,822,340 A | 4/1989 | Kamstra | |
| 4,874,381 A | 10/1989 | Vetter | |
| 4,968,299 A | 11/1990 | Ahlstrand et al. | |
| 5,080,649 A | 1/1992 | Vetter | |
| 5,505,704 A * | 4/1996 | Pawelka et al. | 604/191 |
| 6,053,893 A | 4/2000 | Bucher | |
| 6,419,656 B1 | 7/2002 | Vetter et al. | |
| 6,793,646 B1 | 9/2004 | Giambattista et al. | |
| 2004/0138611 A1* | 7/2004 | Griffiths et al. | 604/82 |
| 2005/0049550 A1* | 3/2005 | Kirchhofer et al. | 604/82 |
| 2005/0049551 A1* | 3/2005 | Kirchhofer | 604/82 |
| 2007/0185439 A1* | 8/2007 | Sugita et al. | 604/82 |

* cited by examiner

*Primary Examiner*—Kevin C Sirmons
*Assistant Examiner*—Michael J Anderson
(74) *Attorney, Agent, or Firm*—Millen, White, Zelano & Branigan, P.C.

(57) ABSTRACT

An injection device is disclosed which is designed to receive therein a two-compartment syringe, and to be used to mix the pharmaceutical agents and then conduct injections. The injection device comprises a cylindrical barrel portion so configured that the two-compartment syringe can be inserted therein in a rear-end first manner, a piston rod for pushing the slidable rear wall to advance, a front spring that is compressed, when the two-compartment syringe is inserted, and then push back the piston rod in the forward direction, and a sleeve which can be shifted back and forth and is provided by screw engagement with the outer surface of the rear part of the barrel portion to block the forward movement of the piston rod.

23 Claims, 3 Drawing Sheets

INJECTION DEVICE

FIELD OF THE INVENTION

The present invention relates to an injection device, in particular to an injection device into which a two-compartment syringe containing pharmaceutical agents in its two compartments separately from each other is loaded, and with which mixing of the pharmaceutical agents and their injection are to be performed.

BACKGROUND OF THE INVENTION

To maintain their stability, injectable peptide preparations, e.g., those of growth hormone, are provided in two-component forms consisting of a dried pharmaceutical component prepared by lyophilization, for example, and a liquid pharmaceutical component (a solvent liquid such as a buffered solution) in which the former component is dissolved to give an injectable liquid. And, to allow patients' easy and reliable handling of them, two-compartment syringes (also called dual-chamber cylinder ampoules) are widely employed, e.g., for human growth hormone preparations, in which those two components are contained separately from each other in a single syringe (FIG. 1).

A two-compartment syringe, as shown in FIG. 1 in a side cross-sectional view, in which the leftward direction represents the actual upward direction, is partitioned in its interior with two slidable walls in a liquid tight fashion (slidable front wall 2 and slidable rear wall 3) to enclose a front space 4 and a rear space 5. In the front space 4, slightly forward of the slidable front wall 2, an elongated longitudinal groove 6 is defined in the inner wall of the two-compartment syringe, which groove has a length enough to stride the thickness of the slidable front wall 2 (therefore being a little longer than the thickness of the slidable front wall 2), so that a bypass through the groove 6 may be created when the whole body of the slideable front wall 2 is placed within the range of the groove 6. In the front space 4 is enclosed a dried pharmaceutical component 10 such as a lyophilized powder, and in the rear space 5 a solvent liquid 11 used to dissolve the dried pharmaceutical component. At the front end of the two-compartment syringe 1, a septum which can be pierced by a double-ended needle, is provided, and, in the figure, a double-ended needle 15 is secured there piercing the septum, and they are covered with a protecting cap 16.

Mixing of the dried pharmaceutical component 10 and the solvent liquid 11 within the two-compartment syringe and injection of them are performed as follows: while the syringe is held with its front end facing upward, with a double-ended needle 15 piercing the septum, the slidable rear wall 3 is pushed in, and by this the slidable front wall 2 is also pushed in. When rear end of the groove 6 is exposed at the rear edge of the slidable front wall 2, a bypass is formed through the groove 6 between the front space 4 and the rear space 5, through which bypass the solvent liquid 11 contained in the rear space 5 begins to be transferred into the front space 4, whereas the slidable front wall 2 comes to a halt there. At the time when the slidable rear wall 3 comes to abut on the slidable front wall 2, all the solvent liquid 11 in the rear space 5 has been transferred into the front space 4 and mixes there with the pharmaceutical component 10 and dissolves it to form an injectable liquid. After this, as the slidable rear wall 3 and the slidable front wall 2 are pushed in a body, the device is handled in the similar manner to conventional one-compartment syringes.

In the case of a peptide hormone preparation, e.g., a growth hormone preparation, a long-term, regular and portionwise repeated administration is needed. Such administration is conducted at home by a patient himself or some other member of the patient's family (hereinafter referred collectively to as "patients"). The patients receive several two-compartment syringes containing undissolved pharmaceutical components together with an injection device into which one of such syringes is to be loaded, and they by themselves perform the processes of mixing of the pharmaceutical components to dissolve within the two-compartment syringe.

The present inventors found that, in the process of mixing the pharmaceutical agents in a two-compartment syringe, which is performed by patients at home, there are some cases in which the slidable rear wall is forcefully and abruptly pushed in, and the necessary cooperation of the front and rear slidable walls 2 and 3 thereby falls short, causing backward leak of the solvent liquid. Thus, there are needs for a device which would guarantee proper mixing of the pharmaceutical agents in a two-compartment syringe, as well as such a device which, in addition, would allow multiple repeated injections of a predetermined volume to be performed properly and easily after mixing. Further, in order to reduce their production cost, it is preferred that such a device could achieve the purpose without relying on a complex structure.

There are known some injection devices which are designed to be used to mix pharmaceutical agents in a two-compartment syringe and perform multiple portionwise injections. However, devices that allow patients to abruptly press in the slidable rear wall in the process of mixing/dissolving of the pharmaceutical agents (see Patent Documents 1 and 2) are not free of the risk of causing the above-mentioned problem of liquid leak. Though such devices are known that are designed so that the piston rod is slowly advanced by rotating a screw and the slidable rear wall is thereby slowly pressed in (see Patent Documents 4 and 5), it is quite troublesome for patients who daily handle such devices that they must rotate the screw with their hand in order to press in the piston rod.

An injection device is known which is provided with a spring to slowly advance the slidable rear wall of a two-compartment syringe (see Patent Document 6). With this device, when the front half of the body of the device holding a two-compartment syringe is inserted deep into the rear half of the body, a lock is released and a cylindrical plunger, being pressed from behind by a spring, is then advanced, which then make the slidable rear wall forwardly advance to mix the contained pharmaceutical agents. After mixing is completed, one of a small number of steps provided in helical arrangement on an injector rod inserted in the rear part of the plunger is positioned on a rib provided in the inside of the plunger and driven to push the latter, and a predetermined amount of the injectable liquid is thereby discharged through the needle. Though this device successfully eliminates the risk of being handled abruptly in mixing of the pharmaceutical agents contained in a two-compartment syringe, it is of a complex structure and consists of a number of components, and, further, it is difficult with this type of device either to provide such steps for adjustment precisely and at short intervals or to make it adapted to repeated multiple portionwise injections, since in the device, control of injection volume is done by engagement of steps provided in a helical arrangement around the thin injector rod with the rib provided in the inside of the plunger. Furthermore, after injection is done with this device, the spring, which is unlocked and extended, and the plunger, which now rests at its foremost position, would not return to their initial positions simply by removing the empty two-compartment syringe or pulling back the injector rod. Therefore, with this injection device, if no improvement is made, it is not easy to restore the initial condition of the device (where the spring is locked), and so the device at least is inconvenient for patients who repeatedly handle it by themselves.

[PATENT DOCUMENT 1] U.S. Pat. No. 4,874,381
[PATENT DOCUMENT 2] U.S. Pat. No. 6,053,893
[PATENT DOCUMENT 3] U.S. Pat. No. 6,419,656
[PATENT DOCUMENT 4] U.S. Pat. No. 4,968,299
[PATENT DOCUMENT 5] U.S. Pat. No. 5,080,649
[PATENT DOCUMENT 6] U.S. Pat. No. 6,793,646

SUMMARY OF THE INVENTION

Against the above-mentioned background, the objective of the present invention to provide an injection device that is designed to receive therein a two-compartment syringe and used to perform a dissolution process of the pharmaceutical agents contained in it and then multiple portionwise injections, wherein the injection device unfailingly prevents the slidable rear wall from being abruptly pressed in during the process of dissolving the contained pharmaceutical agents, thereby guaranteeing proper mixing of the pharmaceutical agents, and then allows multiple portionwise injections of a desired volume, wherein the injection device itself can be repeatedly used by removing an exhausted two-compartment syringe and loading a fresh one, and wherein the injection device makes it easy to adjust the volume to be injected accurately on a smaller scale.

The present inventor found that the above objective can be achieved by providing a piston rod held slidably and supported in the forward direction by a spring, so that, utilizing the repulsive force of the spring, which is compressed via the piston rod once pressed back as a two-compartment syringe is inserted, the slidable rear wall is pushed in by the piston rod to such an extent as needed to dissolve the pharmaceutical agents, and by providing also a stopper whose position is adjusted with a screw-based mechanism, so that any distance of further advancement of the piston rod is controlled by limiting the distance up to which the piston rod can be pushed in. The present invention is accomplished by further studies based on the finding. Thus, the present invention provides what follows.

1. An injection device designed to receive therein a two-compartment syringe having a front end equipped with a septum that can be pierced by a double-ended needle, a cylindrical side wall, a slidable front wall and a slidable rear wall that are liquid-tightly and slidably fitted inside the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall, and to be used to mix, in the two-compartment syringe, the first pharmaceutical component and the second pharmaceutical component and then conduct injection of thus prepared injectable liquid, the injection device comprising, a generally cylindrical barrel portion so configured that the two-compartment syringe can be inserted therein in a rear-end first manner to a predetermined depth, a piston rod for pushing the slidable rear wall from behind to advance the same, the piston rod being placed slidably in the longitudinal direction in the barrel portion, so that it may be pushed forwardly from behind the barrel portion, a front spring provided in the region between the front end of the piston rod and a position which is in the rear of the front end of the piston rod and in intermediate part of the barrel portion, so that, when the two-compartment syringe is inserted into the barrel portion and the front end of the piston rod is thus moved backward by the pressure from the slidable rear wall of the two compartment syringe, the front spring may be compressed and then push back the piston rod in the forward direction, and a sleeve provided at rear part of the barrel portion by screw engagement with the outer surface of the barrel portion, so that the distance of backward extension of the sleeve from the rear end of the barrel portion may be varied by rotating and shifting the same back and forth relative to the barrel portion, wherein the piston rod and the sleeve are so configured and arranged that rear part of the piston rod may abut on the sleeve and be thus prevented from advancing further in the forward direction from the position where it abuts on the sleeve.

2. The injection device as defined in 1 above, wherein the front spring is a coil spring which is placed, with the piston rod passing therethrough.

3. The injection device as defined in 2 above, wherein the front end of the front spring hooks on the head portion of the piston rod.

4. The injection device as defined in 2 or 3 above, wherein the rear end of the front spring is held by a projection provided inside the intermediate part of the barrel portion.

5. The injection device as defined in one of 1 to 4 above, wherein the front spring has sufficient length and strength such that, when the two-compartment syringe is inserted into the barrel portion, with the septum pierced by a double-ended needle to put the front space into communication with the outside, the front spring may be once compressed by the piston rod being moved backward due to the pressure applied by the slidable rear wall of the two-compartment syringe, and then forwardly drive, by its repulsive force, the slidable rear wall via the piston rod to thereby inject the second pharmaceutical component into the front space.

6. The injection device as defined in 2 above, wherein the front spring pushes the slidable rear wall via the piston rod until it abuts on the slidable front wall.

7. The injection device as defined in one of 1 to 6 above further comprising a syringe fastening member configured so as to fasten to the barrel portion the two-compartment syringe inserted to certain depth in a rear-end first manner into the barrel portion, by engaging with the two-compartment syringe and also removably engaging with the barrel portion.

8. The injection device as defined in 7 above, wherein the engagement between the syringe fastening member and the two-compartment syringe is done through the abutment of the shoulder at the front end of the two-compartment syringe on the syringe fastening member.

9. The injection device as defined in 7 or 8 above, wherein the engagement between the syringe fastening member and the barrel portion is done by screw engagement of the syringe fastening member with the surface of the barrel portion.

10. The injection device as defined in one of 1 to 9 above, wherein the barrel portion is further provided with a cylindrical outer wall covering at least front part of the sleeve, and the sleeve is inserted in the gap between the outer wall and the wall of the barrel portion located inside the outer wall.

11. The injection device as defined in 10 above, wherein the outer wall is provided with a sighting means which points to predetermined spots on the outer surface of the sleeve relative to the outer wall, and the outer surface of the sleeve is marked, at each of the spots pointed to by the targeting means corresponding to the amount of the angle of rotation of the sleeve, with a numeral correlated to the amount of the angle of rotation.

12. The injection device as defined in 11 above, wherein the sighting means is a window provided in the outer wall.

13. The injection device as defined in 12 above, wherein the numeral correlated to the amount of the angle of rotation is proportional to the amount of the angle of rotation.

14. The injection device as defined in one of 1 to 13 above, wherein either of the outer wall or the barrel portion, as well as the sleeve, are provided, on one of their opposed surfaces, with equally spaced, longitudinally oriented grooves and, on the other, with a resiliently supported projection which engages in a snap-fit manner with one of the longitudinally oriented grooves and can be disengaged from the groove when the sleeve is rotated.

15. The injection device as defined in one of 1 to 14 above further comprising a rear spring which is placed in the region between the rear end of the piston rod and a position which is in the front of the rear end of the piston rod and in the intermediate part of the barrel portion, the rear spring biasing the piston rod in the backward direction when the position of the piston rod is in the front of the position at which the piston rod brings the slidable rear wall to abut on the slidable front wall.

16. The injection device as defined in 15 above, wherein the rear spring is a coil spring which is placed, with the piston rod passing therethrough.

17. The injection device as defined in one of 1 to 16 above, further comprising an inserted two-compartment syringe.

According to the present invention as defined above, since it is a spring that presses in the slidable rear wall for mixing the pharmaceutical agents in a two-compartment syringe, the slidable rear wall is prevented from being abruptly pressed in, and, thereby, proper mixing of the pharmaceutical agents is guaranteed. And, as the amount of the distance up to which the piston rod is pressed in is controlled by rotating the sleeve which is in screw engagement with the barrel portion, the device makes it easy to perform repeated multiple portion-wise injections, in a predetermined amount, of the injectable liquid prepared by the mixing. Especially, if the device is further provided with a sighting means and the numerals pointed to by it are marked on the sleeve, the device allows a user to visually know with ease the position of the sleeve required to inject a predetermined volume of injection. Further, the injection device of the present invention allows repeated use, and therefore when a two-compartment syringe has been exhausted, the device can be reused with ease, after removing the exhausted two-compartment syringe and inserting a fresh one, for performing mixing of the pharmaceutical agents and then multiple portionwise injections, as done in the first round of injections.

EXPLANATION OF SIGNS

Figure 1:
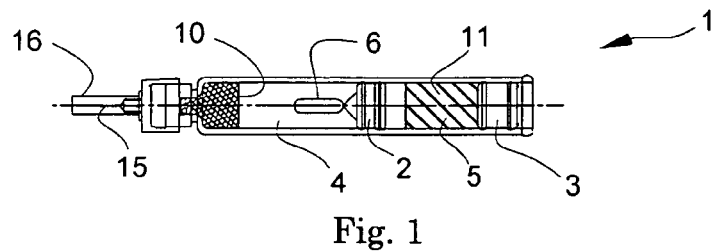
FIG. 1 illustrates a schematic cross sectional view of a two-compartment syringe.

1=two-compartment syringe, 2=slidable front wall, 3=slidable rear wall, 4=front space, 5=rear space, 6=groove, 10=dried pharmaceutical agent, 11=solvent liquid, 15=double-ended needle, 16=protecting cap, 20=injection device, 22, 24=barrel portion, 26=piston rod, 26*h*=head of the piston rod, 26*r*=plate, 30=coil spring, 32=projection, 34=coil spring, 36=sleeve, 38=screw portion, 40=outer wall, 42=rear protecting cap, 44=syringe fastening member, 48=annular projection, 50=shoulder, 52=male screw, 54=rear part of the syringe fastening member, 60=numerals, 62=window, 70=cantilever, 72=longitudinally oriented groove

DETAILED DESCRIPTION OF THE INVENTION

As two-compartment syringes to be inserted in the injection device of the present invention for injection are well known and multiple products are on the market, one of proper sizes of them may be chosen in accordance with the volume of injectable liquid to be mixed and prepared in it, and dimensions of the injection device may be determined in conformity with it.

In the present invention, there is no specific limitation with regard to the shape of the "barrel portion" insofar as it allows insertion of the two-compartment syringe to a predetermined depth in a rear end-first manner and also allows insertion of the piston rod. Although it is preferred that the inside of the front part of the barrel portion in which the a two-compartment syringe is inserted is made in the form of a circular cylinder having the inner diameter slightly greater than the outer diameter of the two-compartment syringe, this is not a requisite and other forms also may be adopted such as those having polygonal, e.g., orthohexagonal, foursquare, or other non-circular cross section that have a size allowing the two-compartment syringe to be accommodated. The shape of the inside of the rear part of the barrel portion may be the same of that of the front part of the barrel portion, though they may differ from each other. In order that the insertion of the two-compartment syringe is blocked when it reaches a predetermined depth, inside the barrel portion may be provided a projection, for example, an annular projection or discrete multiple projections, on which the edge of the rear end of the two-compartment syringe abuts and is prevented from moving rearward. The position of such a projection or projections relative to the front end of the barrel portion may be determined as desired insofar as it does not lead to inconvenience in performing injection, and it may be, for example, a position so that the two-compartment syringe may be blocked from further insertion when three forth of it from its rear end is inserted in the barrel portion.

The length of the piston rod is preferably such that, when the front end of it has been pushed deepest into the two-compartment syringe, the rear end of the piston rod still extends backwardly from the barrel portion. In the present specification, the term "piston rod" means the entire member which is moved back and forth (preferably slides back and forth) in a body, including from the front end which abuts on the slidable rear wall of the two-compartment syringe to the rear end which is pressed from behind the barrel portion. The front spring provided in association with the piston rod is preferably a coil spring and placed in position, with the piston rod passing through it. For the front spring and the piston rod to apply forces to each other, such a structure is preferred that allows the front end of the front spring to engage the piston rod at or near its front end. An example of such a structure is an enlarged front end of the piston rod whose outer diameter there is formed greater than the inner diameter of the front spring, and another example is an annular projection having an outer diameter greater than the inner diameter of the front spring, or a multiple projections projecting up to such an extent, which are provided near the front end of the piston rod. However, this is not a requisite and any proper structure may be adopted as desired. The structure which holds the rear end of the front spring also may be any proper one as desired, for example a projection provided at a desired position inside the intermediate part of the barrel portion (i.e., part between the front end and the rear end of the barrel portion, and preferably a central portion). Such a projection may be one of the aforementioned projections that block rearward movement of the two-compartment syringe, and in this case, the top of the projection may extend inwardly, beyond the wall thickness of the two-compartment syringe and at least to the inside of the outer diameter of the front spring, thereby providing an area to engage with the rear end of the front spring. It is also possible to provide, alternatively, another projection located to the rearward to engage with the rear end of the front spring.

The length and strength of the front spring may be determined so that they may be sufficient to push in the slidable rear wall of the two-compartment syringe to also drive the slidable front wall up to the position of the bypass and then transfer the solvent liquid contained in the rear space to the front space by the repulsive force created by temporary retraction and compression of the front spring which is pushed, via the head of the piston rod, by the slidable rear wall of the two-compartment syringe, as the two-compartment syringe is inserted into the barrel portion. The length and strength of the front spring can be readily chosen based, for example, on the position at which the slidable rear wall is to abut on the slidable front wall within the inserted two-compartment syringe, and the amount of the force required to push in the slidable rear wall up to that position. For example, with the front space being in communication via the bypass with the rear space, the front spring is only required to drive the slidable rear wall alone against the frictional force between it and the inner surface of the two-compartment syringe. After the slidable rear wall abuts on the slidable front wall, however, the fictional force between the two slidable walls and the inner surface of the two-compartment syringe resists the repulsive force of the spring for any further advancement of the slidable rear walls. Therefore, the strength of the spring is determined so as not to drive the both slidable walls from that position. Meanwhile, at the stage before the front space comes into communication with the rear space, though the advancement of the slidable rear wall is accompanied by that of the slidable front wall, the front spring is capable of pressing the slidable rear wall with a sufficient strength of force to push in the both slidable walls, for the spring, at this stage, is in more compressed state.

According to the above configuration, by inserting a two-compartment syringe in the barrel portion, with the septum opening to the outside through an injection needle, the slidable rear wall, being pushed by the repulsive force of the spring once compressed, advances and causes the solvent liquid to be transferred to the front space, thereby preparing the injection liquid through mixing of the pharmaceutical agents. Due to the frictional force between the sidable rear wall (or also the slidable front wall, before the bypass is open) and the inner surface of the two-compartment syringe, any abrupt advancement of the slidable rear wall is prevented when the slidable rear wall is pressed in by the front spring. Therefore, a proper mixing process of the pharmaceutical agents in the two-compartment syringe is performed without fail.

In order to connect the barrel portion with the movable sleeve provided at the rear part of it by screw engagement, corresponding male or female screw may be formed on each of them. Such corresponding male or female screw not necessarily has a completely continuous helical thread insofar as it meets purpose of screw engagement. For example, one of them has a completely continuous helical thread and the other consists of multiple projections arranged to engage the former. As the sleeve in screw engagement with the barrel portion can be rotated by hand, its position in the longitudinal direction can be varied by so doing relative to the barrel portion. Thus, the rear end of the sleeve can be placed projecting rearward from the rear end of the barrel portion, with the extent of such projection being adjustable with the amount of the angle of rotation of the sleeve.

The sleeve works as a stopper which, corresponding to its own position, limits the range within which the piston rod can move. For this, the rear part of the piston rod and the sleeve may be given such mutual forms that, when the piston rod is to be driven forward, some portion of rear part of the piston rod abuts on some portion of the sleeve, and thereby further advancement of the piston rod is blocked. Such forms are determined as desired. For example, but not limited to, the piston rod may be provided with a projection near the rear end of it, or its rear end may be formed into a plate with an enlarged diameter. It is preferable that, in the process of designing, the position at which the piston rod abuts on the sleeve is set in accordance with a two-compartment syringe which is to be inserted so that expulsion of air from the two-compartment syringe may have been completed when the piston rod is pressed from behind until it is blocked by the sleeve, with the sleeve projecting rearward at the maximum. As a preparation for injection contains a volume which is greater than its nominal volume on the assumption that some of the volume will be lost when air is expelled, this adjustment may be made so that the very nominal volume of the two-compartment syringe may be discharged as the piston rod advances from its position at which the expulsion of air is completed to its deepest position.

In the present invention, the structure of the syringe fastening member for fastening the two-compartment syringe inserted in the barrel portion is not limited insofar as it engages with both of the two-compartment syringe and the barrel portion. To achieve engagement between the syringe fastening member and the two-compartment syringe, for example, the form of the syringe fastening member is determined so that it abuts on the shoulder at the front end of the two-compartment syringe (i.e., the circumference edge at the front end of the cylindrical body of the syringe). For this, for example, the front part of the syringe fastening member may be made in a cylindrical form which fit the front part of the two-compartment syringe, and is provided with an inward projection (e.g., annular projection) on the inner circumference edge at its front end. The engagement between the syringe fastening member and the barrel portion may also be made in any manner as desired. For example, rear part of the syringe fastening member may be made to screw-engage with the outer surface or the inner surface (in the specification, an "outer surface" and an "inner surface" are referred collectively as a "surface") of the barrel portion of the injection device. This is performed, for example, by making the rear part of the syringe fastening member in a cylindrical form of the sizes which allow accommodation of the barrel portion and forming a female thread on its inner surface, and further forming a male thread on the corresponding area of the outer surface of the barrel portion, so that the rear part of the syringe fastening member may be screwed on the outer surface of the barrel portion. Alternatively, the rear part of the syringe fastening member may be made to screw-engage, from inside, with the inner surface of the front end part of the barrel portion of the injection device. This may be performed, for example, by making the rear part of the syringe fastening member in a cylindrical form of the same diameter as its front part and forming a male thread on the outer surface of the rear part, and further making, at least front part of the barrel portion, in a cylindrical form of the sizes allowing accommodation of the rear part of the syringe fastening member, as well as forming a female thread, which corresponds to the male thread of the syringe fastening member, on the inner surface of the front part of the barrel portion.

It is preferable to provide a rear spring for backwardly biasing the piston rod. If it is provided, since the rear spring is for the purpose of biasing the piston rod back to its initial position when the piston rod is pressed forward beyond that position where the piston rod brings the slidable rear wall into abutment on the slidable front wall, it is not required that the rear spring bias the piston rod further backwardly beyond the initial position. Provision of a rear spring allows the piston rod to project backwardly always to nearly the same extent before it is pressed in at each of the multiple portionwise injections. The rear spring is preferably a coil spring, and placed in position, with the piston rod passing through it. For the rear spring and the piston rod to apply force to each other, for example, in order that the rear end of the rear spring abut on the piston rod at a certain position determined as desired, the piston rod may be given, in the rear of the positions, an outer diameter greater than the inner diameter of the rear spring or the piston rod may be provided at that position with an annular projection having an outer diameter greater than the inner diameter of the rear spring or, alternatively, multiple projections projecting up to such a height. The structure which holds the front end of the rear spring may be determined as desired, ant it may be, for example, a projection provided as desired at a position inside the intermediate part of the barrel portion. Such a projection may be the same as the projection holding the rear end of the front spring or another projection provided to the rearward of it.

Though the length of the front spring and the rear spring may be determined as desired, it is preferred that when one of them is at its natural length, the other is also nearly at its natural length or in a slightly compressed state. This is because such an arrangement, through the balance of the forces of them, serves, in each injection, to stabilize the position of the piston rod before it is pushed in.

It is preferable to provide the barrel portion with a cylindrical outer wall covering at least front part of the sleeve. This is because an outer wall thus provided will prevent, at each occasion of injection, the sleeve from being inadvertently rotated by fingers which are holding the barrel portion as the piston rod is pushed in. In addition, an outer wall is preferably provided with a sighting means which points to certain spots on the outer surface of the sleeve. A "sighting means" may be in any form insofar as it identifies spots on the outer surface of the sleeve brought to a predetermined position relative to the outer wall, as the sleeve which is forwardly advanced by being rotated by hand. Examples of such a sighting means include a vertical line, a notch or a triangular projection which is marked or formed, pointing to the outer surface of the sleeve, at a position on the edge of the outer wall, and a window (e.g., a through bore) which is formed at a position of the outer wall and having a diameter that allows to view through it the outer surface of the sleeve, and the like. By marking, for each fixed increment of the angle of rotation of the sleeve, each spot (on the outer surface of the sleeve) that comes to be pointed to by the sighting means, corresponding to the amount of the angle of rotation, with a certain numeral correlated with the angle of rotation (e.g., a numeral indicating the very amount of the angle of rotation itself, or a numeral indicating the longitudinal position determined by the angle of rotation, or other numerals correlated in any desired manner, such as a number that is proportional to the angle of rotation with a coefficient chosen as desired, and the like), it is made easy for a physician in charge to direct the user (patient) to what degree he or she should rotate the sleeve (this will set the injection volume each time) each time before he or she performs injection. Among those numerals, the starting point ("zero" point) may be marked, for example, at the spot on the outer surface of the sleeve which is pointed to by the sighting means when the sleeve is projecting backward at its maximum.

Although the sleeve may be such a one that can be rotated at any desired angle, it is preferable that it may be brought to stop at any one of predetermined angles in a snap-fit manner. This can be made by, for example, forming longitudinally oriented grooves in one of the opposed surfaces of the sleeve and the outer wall (or of the barrel portion), and providing the other with a resiliently supported projection which engages the former in a snap-fit manner. By this, adjustment of the angle of rotation each time can be stabilized, for the sleeve engages with the outer wall, or the barrel portion, at each of the predetermined angles in a snap-fit manner. Such a resiliently supported projection may be provided by, for example, forming, close to the front end of the sleeve, a cantilever which can be resiliently bent on which a projection, e.g. one having a triangular cross section, which can engage in a snap-fit manner with a longitudinally oriented groove formed in the surface of the counterpart outer wall (or the barrel portion). Such a cantilever may be provided, for example, as forwardly protruding from the front end of the sleeve or, alternatively, formed by a generally U-shaped slit cut in the outer surface of the sleeve at a certain position. Contrarily, it is also possible to form longitudinally oriented grooves in the outer or inner surface of the sleeve and to provide a resiliently supported projection on the opposed surface of the outer wall or the barrel portion, so that they engage with each other in a snap-fit manner. If a sighting means as aforementioned is provided, the position of the projection and the number and the positions of the longitudinally oriented grooves are determined so that each of the numerals marked on the outer surface of the sleeve comes at the position pointed to by the sighting means, when the resiliently supported projection and one of the longitudinally oriented grooves come to engage with each other in a snap-fit manner.

EXAMPLES

The present invention is described in further detail below with reference to a typical example. However, it is not intended that the present invention be limited to the example.

Figure 2:
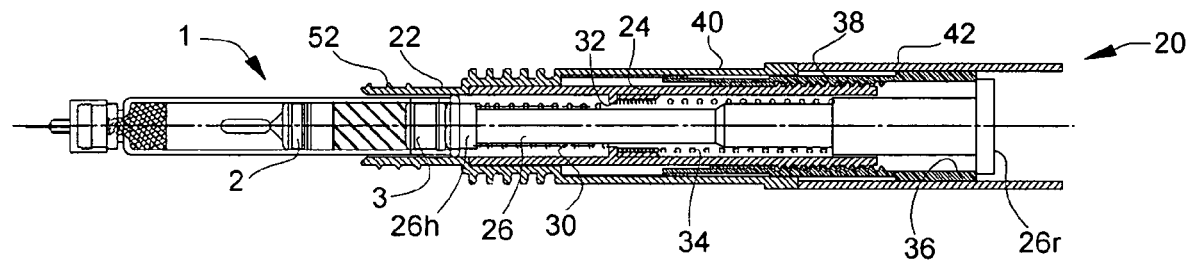
FIG. 2 illustrates a cross sectional view of an injection device, into which a two-compartment syringe is just being inserted.
Figure 3:
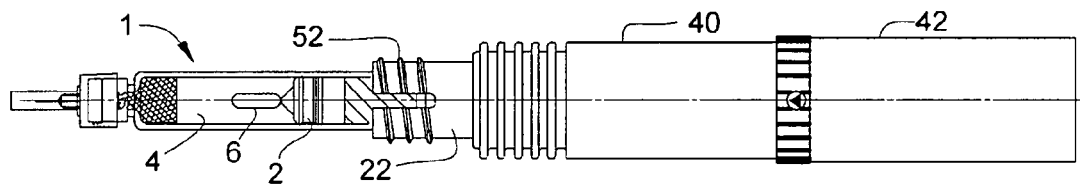
FIG. 3 illustrates a side view of the injection device, into which a two-compartment syringe is just being inserted.

FIG. 2 illustrates a cross section of the injection device 20 in the example, with the two-compartment syringe shown in FIG. 1 just starting to be inserted in a rear end-first manner, and FIG. 3 illustrates a side view of it. With regard to these figures, the leftward direction in the drawing represents the upward direction in actual operation. In FIG. 2, both of those indicated with numerals 22 and 24 are cylindrical and parts of the barrel portion, which, combined together, form a cylindrical barrel portion. A piston rod 26 is passed through the barrel portion. The piston rod 26 includes a head 26h having an enlarged diameter formed at and near the front end, and a plate 26r having an enlarged diameter formed at the rear end. In association with the piston rod 26, a coil spring 30 (front spring) is placed in the rear of the head 26h. In the figure, the front end of the coil spring 30 abuts on the edge of the head 26h of the piston rod, and the rear end of it abuts on and is held by the front face of an annular projection 32 which is provided inside the intermediate part of the barrel portion. The slidable rear wall 3 of the two-compartment syringe 1 abuts on the head 26h of the piston rod, and the piston rod 26 is about to be pressed backward as the two-compartment syringe is inserted. In the rear of the projection 32, another coil spring 34 (rear spring) is placed in association with the piston rod 26. In the situation illustrated in the figure, the front end of the rear spring 34 is held by its abutment on the rear face of the projection 32 and also by being griped by a portion having an increased thickness of the wall formed in the inner surface of the barrel portion in the rear of the projection 32.

With the rear part of the barrel portion, a sleeve 36 engages by screw engagement via a screw portion 38. The rear end of the sleeve 36 abuts on the edge of the plate 26r at the end of the piston rod, and works as a stopper which blocks the piston rod 26 from advancing forward. The sleeve 36 can be moved back and forth by rotating it by hand relative to the barrel portion, and in the figure, it is at its most retracted position.

The barrel portion is provided with a cylindrical outer wall 40 covering front part of the sleeve 36, and the sleeve 36 is inserted, at its front part, in the gap between the outer wall 40 and the wall of the barrel portion which is placed inside the outer wall. In the rear of the outer wall 40, there is a cylindrical rear protecting cap 42 which covers the sleeve 36 from outside. The rear protecting cap 42 is provided in order to protect the piston rod 26, when it temporarily protrudes backward in the process of mixing of the pharmaceutical agents in the two-compartment syringe as mentioned below, and it can be removed by pulling it backward by hand.

Figure 4:
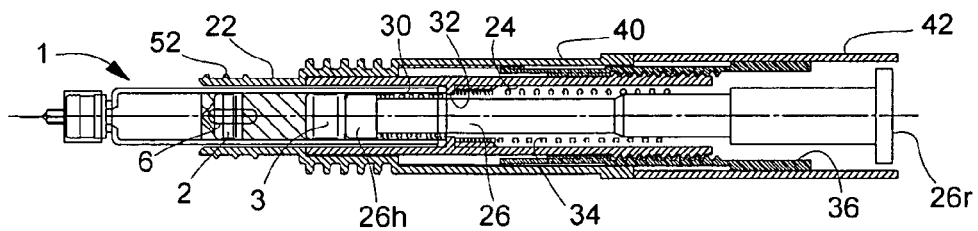
FIG. 4 illustrates a cross sectional view showing the injection device immediately after the two-compartment syringe is inserted deepest into the barrel portion.

FIG. 4 illustrates a cross sectional view showing the injection device immediately after the two-compartment syringe is inserted deepest into the barrel portion and stopped there. The leftward direction in the drawing represents the upward direction in actual operation. In the figure, the piston rod 26 is retracted from the position shown in FIG. 2, and thereby the plate 26r at the rear end is away from the rear end of the sleeve 36. The front spring 30 is compressed between the head 26h of the retracted piston rod and the projection 32 in the barrel portion, but at the same time, by its repulsive force, pushing via the head 26h of the piston rod, the slidable rear wall 3 of the two-compartment syringe 1, and thereby causing the solvent liquid to be injected into the front space 4 through the groove 6 (bypass).

Figure 5:
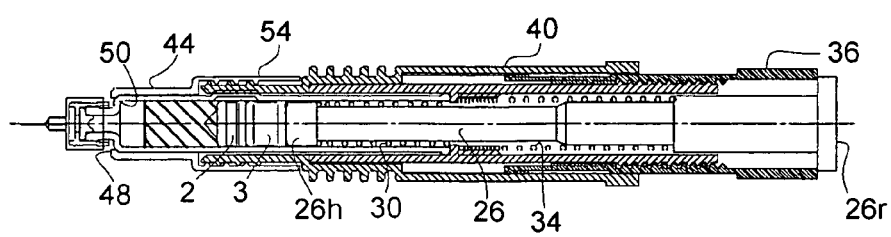
FIG. 5 illustrates a cross sectional view of the injection device to which is attached a syringe fastening member and from which the rear protecting cap has been pulled off.

FIG. 5 illustrates a cross sectional view of the injection device to which is attached a syringe fastening member and from which the rear protecting cap 42 has been pulled off. The syringe fastening member 44 has an internal annular projection 48 in the front inner edge of a cylindrical portion having an inner diameter which the two-compartment syringe fits, and the internal annular projection engages with the shoulder 50 at the front end of the two-compartment syringe 1. And then, the syringe fastening member 44, by securing itself at its rear part 54, which has a female screw which engages with the male screw 52 formed on the outer surface of front part of the barrel portion, to the barrel portion, fastens the two-compartment syringe 1 so that it will not drop off forwardly. In the stage illustrated in FIG. 5, the piston rod 26 is pushed into the two-compartment syringe by the repulsive force of the front spring 30 until it brings the slidable rear wall 3 into abutment on the slidable front wall 2 of the two-compartment syringe.

Figure 6:
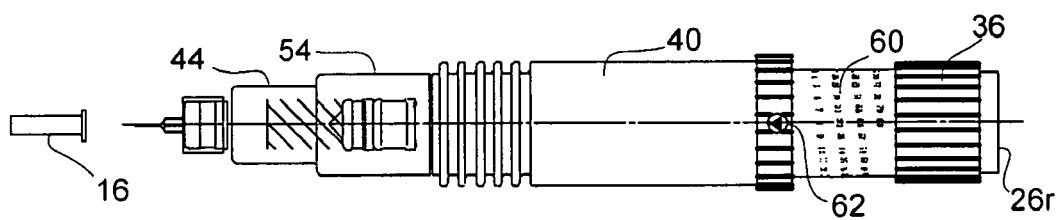
FIG. 6 illustrates a side view of the injection device to which is attached a syringe fastening member and from which the rear protecting cap has been pulled off.
Figure 7:
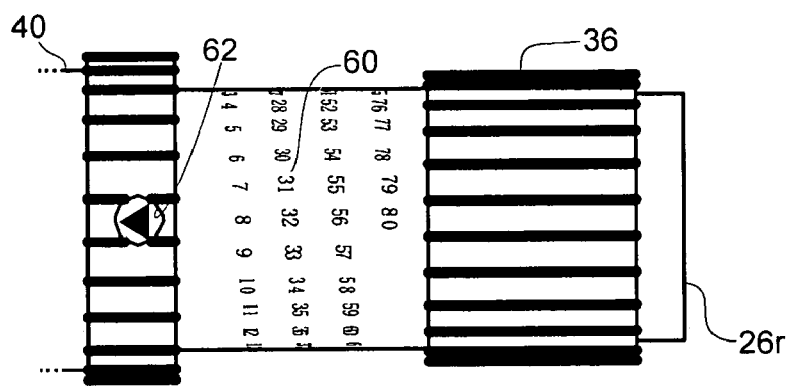
FIG. 7 illustrates an enlarged side view of the device around the sleeve in the position shown in FIG. 5.

FIG. 6 illustrates a side view of the injection device in the situation shown in FIG. 5, and FIG. 7 illustrates an enlarged side view of the device around the sleeve 36 in the situation shown in FIG. 5. As seen in these figures, the outer surface of the sleeve 36 is marked with multiple numerals 60 increasing in the increment of one, which are arranged in a helical form and equally spaced. A window 62 is formed in the outer wall 40 near its end covering a front part of the sleeve 36, and through the window is seen a sign (closed triangle) marked on the outer surface of the sleeve 36. The sleeve 36 engages with the barrel portion with a right hand screw, and the pitch of the helix formed by the multiple numerals is made equal to that of the female screw of the sleeve 36. The aforementioned sign is on extrapolated part of the helix formed by the numerals 60, and the device is so configured that the initial numeral "0" appears in the window 62 when the sleeve is rotated clockwise.

Figure 8:
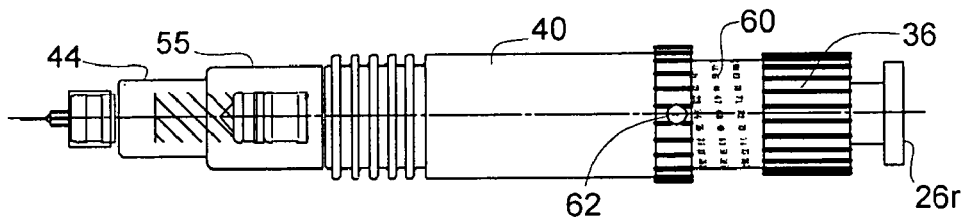
FIG. 8 illustrates a side view of the injection device when the numeral "0" is made to appear in the window.
Figure 9:
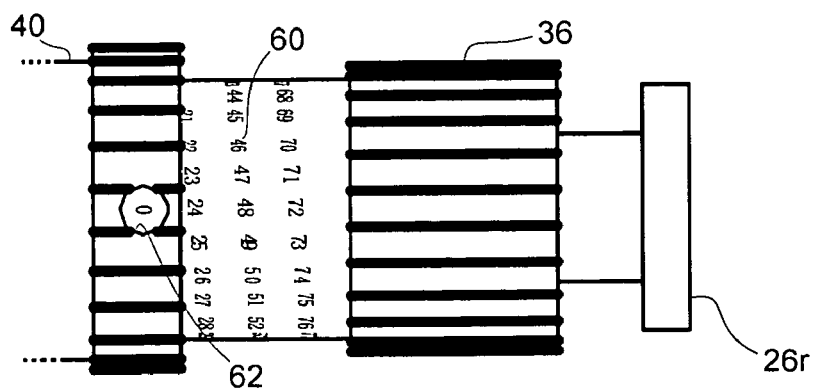
FIG. 9 illustrates an enlarged side view around the sleeve at the position shown in FIG. 8.
Figure 10:
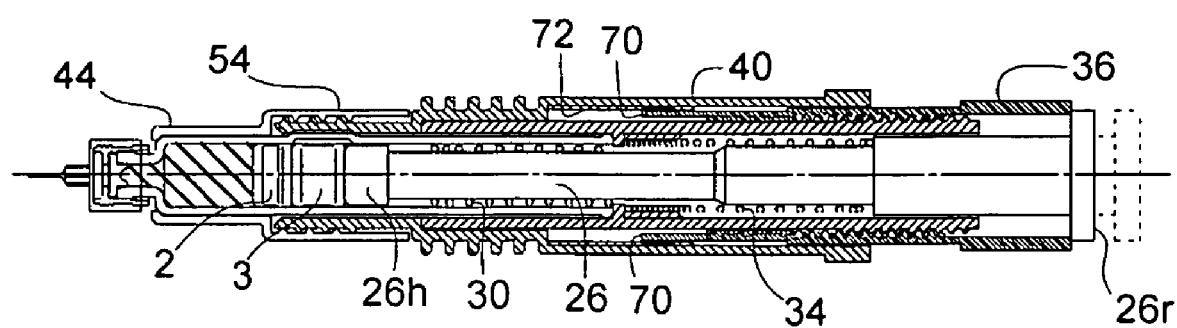
FIG. 10 illustrates a cross sectional view of the injection device shown in FIG. 8.

FIG. 8 illustrates a side view of the injection device when the sleeve is rotated and the numeral "0" appears in the window 62, FIG. 9. an enlarged side view around the sleeve 36 at the situation, and FIG. 10 a cross sectional view of the injection device at the same situation. The position of the sleeve when the numeral "0" appears in the window 62 is set in advance so that, when the piston rod 26 is pushed in until it is blocked by the sleeve 36 in that position, expulsion of air from the two-compartment syringe is just completed and the piston is now at the initial position that allows injection, as shown in FIG. 10. In the example illustrated in the figure, the numerals 60 arranged in a helical form are marked so as to divide the 360° around the outer circumference of the sleeve 36 into 24 equal portions. Therefore, starting from the position where the numeral "0" appears in the window 62, when the sleeve 36 is rotated clockwise until a numeral "i" appears in the window, the amount of rotation of the sleeve 36 is the amount of the angle corresponding to the difference "i", i.e., 15×i (°). The same is true when the sleeve 36 is rotated between other numerals. The sleeve 36, when rotated clockwise, advances a fraction of the pitch of the screw portion 38 corresponding to the angle of rotation, and thus allows the piston rod 26 to be further pushed in the same amount, thereby injecting a fixed volume. Therefore, the user of the injection device can inject a predetermined volume at each injection, by rotating the sleeve 36 clockwise by an increment indicated in advance by the doctor in charge, then piecing the body with the needle 15, and pushing the piston rod 26. Thought, in the example illustrated in the figure, the marking with the numerals are made dividing the 360° into 24 equal portions, it is also possible to place the numerals in any other manner as desired, for example, dividing the circumference into 12 or 6 equal portions.

With regard to the adjustment of injected volumes based on the amount of the angle of rotation of the sleeve 36, a pair of cantilevers 70, which are biases laterally and each of which has a laterally projecting projection of a triangular cross section, extend forwardly from the front end of the sleeve 36, and the tips of the projections engage with corresponding ones of the 24 longitudinal oriented grooves 72 formed in the internal surface of the outer wall 40 in a snap-fit manner. The mutual positioning of the projections on the cantilevers 70 and the longitudinally oriented grooves 72 are made so that, when they engage with each other, one of the numerals marked on the outer surface of the sleeve 36 may appear in the window 62 in the outer wall 40. When the sleeve 36 is rotated by hand, the projections disengage themselves, against slight resistance, from the grooves with which they currently engage and move to the adjacent grooves and then engage with them. Therefore, it is guaranteed that the angle of rotation of the sleeve 36 is always set at one of predetermined angles of rotation, and thereby the angle of rotation is made free of fluctuation.

Thus, the patient can easily perform injection of a predetermined volume of injection liquid repeatedly at each time for injection, by rotating the sleeve 36 by a predetermined amount of angle and then pushing the piston rod. When the injectable liquid in the two-compartment syringe 1 has been exhausted, the syringe fastening member 44 is disengaged and the empty two-compartment syringe is removed, and the sleeve 36 is rotated counterclockwise back to its initial position. Then, inserting a fresh two-compartment syringe in the manner as described above, exactly the same procedure as above can be followed to resume the process of injection.

INDUSTRIAL APPLICABILITY

The present invention is useful as an easy-to-handle, convenient injection device which guarantees proper mixing of the pharmaceutical agents contained in a two-compartment syringe, makes it easy to perform repeated injections of a predetermined volume of the injectable liquid, and can be reused repeatedly by replacing an exhausted two-compartment syringe with a fresh one.

Without further elaboration, it is believed that one skilled in the art can, using the preceding description, utilize the present invention to its fullest extent. The preceding preferred specific embodiments are, therefore to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated The entire disclosures of all applications, patents and publications, cited herein and of corresponding Japanese application No. JP 2005-344094, filed Nov. 29, 2005, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An injection device designed to receive therein a two-compartment syringe having a front end equipped with a septum that can be pierced by a double-ended needle, a cylindrical side wall, a slidable front wall and a slidable rear wall that are liquid-tight and slidably fitted inside the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall, and to be used to mix, in the two-compartment syringe, the first pharmaceutical component and the second pharmaceutical component and then conduct injection of thus prepared injectable liquid, the injection device comprising, a generally cylindrical barrel portion so configured that the two-compartment syringe can be inserted therein in a rear-end first manner to a predetermined depth, a piston rod for pushing the slidable rear wall from behind to advance the same, the piston rod being placed slidably in the longitudinal direction in the barrel portion, so that it may be pushed forwardly from behind the barrel portion, a front spring provided in the region between the front end of the piston rod and a position which is in the rear of the front end of the piston rod and an intermediate part of the barrel portion, so that, when the two-compartment syringe is inserted into the barrel portion and the front end of the piston rod is thus moved backward by the pressure from the slidable rear wail of the two compartment syringe, the front spring may be compressed and then push back the piston rod in the forward direction, and a sleeve provided at rear part of the barrel portion by screw engagement with the outer surface of the barrel portion, so that the distance of backward extension of the sleeve from the rear end of the barrel portion may be varied by rotating and shifting the same back and forth relative to the barrel portion, wherein the piston rod and the sleeve are so configured and arranged that the rear part of the piston rod may abut on the sleeve and be thus prevented from advancing further in the forward direction from the position where it abuts on the sleeve.

2. The injection device of claim 1, wherein the front spring is a coil spring which is placed, with the piston rod passing therethrough.

3. The injection device of claim 2, wherein the front end of the front spring hooks on the head portion of the piston rod.

4. The injection device of claim 2, wherein the rear end of the front spring is held by a projection provided inside the intermediate part of the barrel portion.

5. The injection device of claim 1, wherein the font spring has sufficient length and strength such that, when the two-compartment syringe is inserted into the barrel portion, with the septum pierced by a double-ended needle to put the front space into communication with the outside, the front spring may be once compressed by the piston rod being moved backward due to the pressure applied by the slidable rear wall of the two-compartment syringe, and then forwardly drive, by its repulsive force, the slidable rear wall via the piston rod to thereby inject the second pharmaceutical component into the front space.

6. The injection device of claim 2, wherein the front spring pushes the slidable rear wall via the piston rod until it abuts on the slidable front wall.

7. The injection device of claim 1 further comprising a syringe fastening member configured so as to fasten to the barrel portion the two-compartment syringe inserted to certain depth in a rear-end first manner into the barrel portion, by engaging with the two-compartment syringe and also removably engaging with the barrel portion.

8. The injection device of claim 7, wherein the engagement between the syringe fastening member and the two-compartment syringe is done through the abutment of the shoulder at the front end of the two-compartment syringe on the syringe fastening member.

9. The injection device of claim 7, wherein the engagement between the syringe fastening member and the barrel portion is done by screw engagement of the syringe fastening member with the surface of the barrel portion.

10. The injection device of claim 1, wherein the barrel portion is further provided with a cylindrical outer wall covering at least front part of the sleeve, and the sleeve is inserted in the gap between the outer wall and the wall of the barrel portion located inside the outer wall.

11. The injection device of claim 10, wherein the outer wall is provided with a sighting means which points to predetermined spots on the outer surface of the sleeve relative to the outer wall, and the outer surface of the sleeve is marked, at each of the spots pointed to by the targeting means corresponding to the amount of the angle of rotation of the sleeve, with a numeral correlated to the amount of the angle of rotation.

12. The injection device of claim 11, wherein the sighting means is a window provided in the outer wall.

13. The injection device of claim 12, wherein the numeral correlated to the amount of the angle of rotation is proportional to the amount of the angle of rotation.

14. The injection device of claim 1, wherein either of the outer wall or the barrel portion, as well as the sleeve, are provided, on one of their opposed surfaces, with equally spaced, longitudinally oriented grooves and, on the other, with a resiliently supported projection which engages in a snap-fit manner with one of the longitudinally oriented grooves and can be disengaged from the groove when the sleeve is rotated.

15. The injection device of claim 1 further comprising a rear spring which is placed in the region between the rear end of the piston rod and a position which is in the front of the rear end of the piston rod and in the intermediate part of the barrel portion, the rear spring biasing the piston rod in the backward direction when the position of the piston rod is in the front of the position at which the piston rod brings the slidable rear wall to abut on the slidable front wall.

16. The injection device of claim 15, wherein the rear spring is a coil spring which is placed, with the piston rod passing therethrough.

17. The injection device of claim 1, further comprising an inserted two-compartment syringe.

18. An injection device designed to receive therein a two-compartment syringe having a front end equipped with a septum that can be pierced by a double-ended needle, a cylindrical side wall, a slidable front wall and a slidable rear wall that are liquid tight and slidably fitted inside the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall, and to be used to mix, in the two-compartment syringe, the first pharmaceutical component and the second pharmaceutical component and then conduct injection of thus prepared injectable liquid, the injection device comprising, a generally cylindrical barrel portion so configured that the two-compartment syringe can be inserted therein in a rear-end first manner to a predetermined depth, a piston rod having a front end engaging the slidable rear wall for pushing the slidable rear wall from behind to advance the same, the piston rod being placed slidably in the longitudinal direction in the barrel portion to be pushed forwardly from behind the barrel portion, an initially uncompressed front spring provided in the region between the front end of the piston rod and a position which is in the rear of the front end of the piston rod in an intermediate part of the barrel portion, so that, when the two-compartment syringe is inserted into the barrel portion and the front end of the piston rod is thus moved backward by the pressure from engagement with the slidable rear wall of the two compartment syringe, the front spring is compressed by the slidable rear wall and then pushes the piston rod in the forward direction, and a sleeve provided at rear part of the barrel portion by screw engagement with the outer surface of the barrel portion, so that the distance of backward extension of the sleeve from the rear end of the barrel portion may be varied by rotating and shifting the same back and forth relative to the barrel portion, wherein the piston rod and the sleeve are so configured and arranged that the rear part of the piston rod may abut on the sleeve and he thus prevented from advancing further in the forward direction from the position where it abuts on the sleeve.

19. The injection device of claim 18, wherein the front spring is a coil spring with the piston rod passing therethrough.

20. The injection device of claim 19, wherein the front end of the front spring is connected to the head portion of the piston rod.

21. The injection device of claim 19, wherein the rear end of the front spring is held by a projection provided inside the intermediate part of the barrel portion.

22. The injection device of claim 18, wherein the front spring has sufficient length and strength such that, when the two-compartment syringe is inserted into the barrel portion, with the septum pierced by a double-ended needle to put the front space into communication with the outside, the front spring may be once compressed by the piston rod being moved backward due to the pressure applied by the slidable rear wall of the two-compartment syringe, and then forwardly drive, by its repulsive force, the slidable rear wall via the piston rod to thereby inject the second pharmaceutical component into the front space.

23. The injection device of claim 19, wherein the front spring pushes the slidable rear wall via the piston rod until it abuts on the slidable front wall.

* * * * *

UNITED STATES PATENT AND TRADEMARK OFFICE
CERTIFICATE OF CORRECTION

PATENT NO. : 7,534,222 B2
APPLICATION NO. : 11/604900
DATED : May 19, 2009
INVENTOR(S) : Sugita et al.

It is certified that error appears in the above-identified patent and that said Letters Patent is hereby corrected as shown below:

Column 14, line 33 reads "pressure from the slidable rear wail of the two compart-", should read -- pressure from the slidable rear wall of the two compare- --.

Signed and Sealed this

Seventeenth Day of November, 2009

David J. Kappos
*Director of the United States Patent and Trademark Office*